(12) United States Patent
Chaudhry et al.

(10) Patent No.: US 9,638,588 B2
(45) Date of Patent: May 2, 2017

(54) MULTIFUNCTIONAL LOAD AND DAMAGE SENSOR

(71) Applicant: Sikorsky Aircraft Corporation, Stratford, CT (US)

(72) Inventors: Zaffir A. Chaudhry, S. Glastonbury, CT (US); Fanping Sun, Glastonbury, CT (US); Avinash Sarlashkar, Pittsford, NY (US)

(73) Assignee: SIKORSKY AIRCRAFT CORPORATION, Stratford, CT (US)

( * ) Notice: Subject to any disclaimer, the term of this patent is extended or adjusted under 35 U.S.C. 154(b) by 98 days.

(21) Appl. No.: 14/201,152

(22) Filed: Mar. 7, 2014

(65) Prior Publication Data
US 2015/0253209 A1 Sep. 10, 2015

(51) Int. Cl.
| G01L 1/16 | (2006.01) |
|---|---|
| G01M 5/00 | (2006.01) |
| G01N 29/11 | (2006.01) |
| G01N 29/24 | (2006.01) |

(52) U.S. Cl.
CPC ............ *G01L 1/16* (2013.01); *G01M 5/0025* (2013.01); *G01N 29/11* (2013.01); *G01N 29/245* (2013.01); *G01N 29/2475* (2013.01); *G01N 2291/02827* (2013.01); *G01N 2291/2694* (2013.01)

(58) Field of Classification Search
CPC ........................................................ G01L 1/16
See application file for complete search history.

(56) References Cited

U.S. PATENT DOCUMENTS

| 4,680,470 | A * | 7/1987 | Heald | G21C 17/002 250/358.1 |
|---|---|---|---|---|
| 4,766,769 | A * | 8/1988 | Nudd, Jr. | G01L 9/0054 73/706 |
| 6,768,312 | B2 * | 7/2004 | Sun | G01N 29/09 324/509 |
| 6,845,672 | B2 * | 1/2005 | Mol | G01L 5/0009 73/593 |
| 7,311,009 | B2 * | 12/2007 | Kotovsky | G01L 1/18 438/50 |
| 7,458,266 | B2 * | 12/2008 | Beard | G01N 29/043 702/39 |
| 7,571,058 | B2 * | 8/2009 | Sealing | H04Q 9/00 702/34 |
| 7,738,730 | B2 * | 6/2010 | Hawley | G06K 9/4633 382/278 |
| 7,953,561 | B2 * | 5/2011 | Musial | G01M 7/00 702/141 |

(Continued)

OTHER PUBLICATIONS

International Search Report for application PCT/US15/18717, dated Jun. 25, 2015, 6 pages.

(Continued)

*Primary Examiner* — Lisa Caputo
*Assistant Examiner* — Tran M Tran
(74) *Attorney, Agent, or Firm* — Cantor Colburn LLP

(57) ABSTRACT

Embodiments are directed to obtaining at least one sample of load or load path data from at least one piezoelectric sensor associated with a structure, comparing the at least one sample of data to at least one prior sample of data obtained from the at least one sensor, and providing a status of a health of the structure based on the comparison.

19 Claims, 5 Drawing Sheets

(56) References Cited

U.S. PATENT DOCUMENTS

| | | | |
|---|---|---|---|
| 8,366,045 B2* | 2/2013 | Goncalves De Oliveira | G01L 1/06 244/108 |
| 8,694,235 B2* | 4/2014 | Eadie ............ | B64D 9/00 701/124 |
| 2007/0006652 A1* | 1/2007 | Weldon, Jr. ............ | G01G 3/16 73/579 |
| 2008/0011091 A1* | 1/2008 | Weldon, Jr. ............ | G01L 1/255 73/766 |
| 2009/0319165 A1 | 12/2009 | Eadie | |
| 2010/0161244 A1* | 6/2010 | Ghoshal ............ | G01N 29/14 702/35 |
| 2011/0264310 A1* | 10/2011 | Bates ............ | G07C 5/085 701/14 |

OTHER PUBLICATIONS

PCT Written Opinion for application PCT/US15/18717, dated Jun. 25, 2015, 5 pages.

* cited by examiner

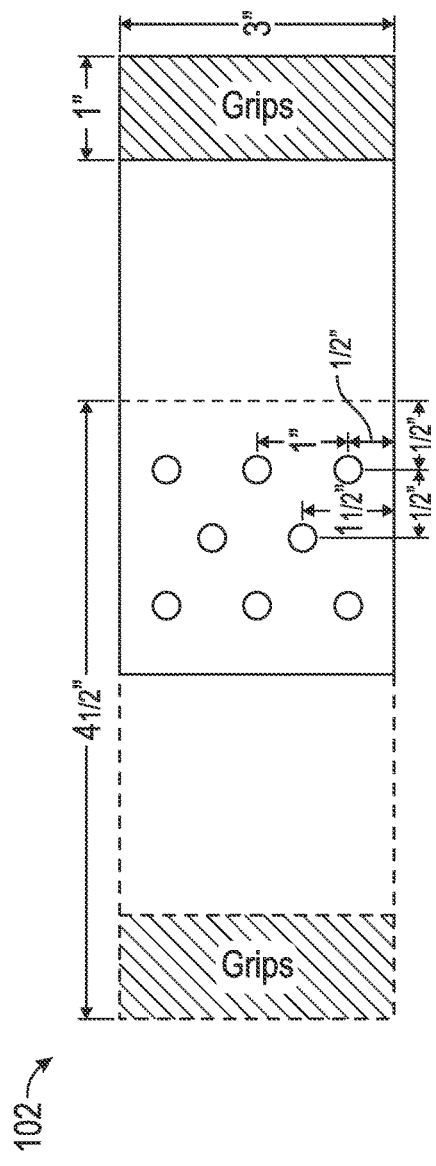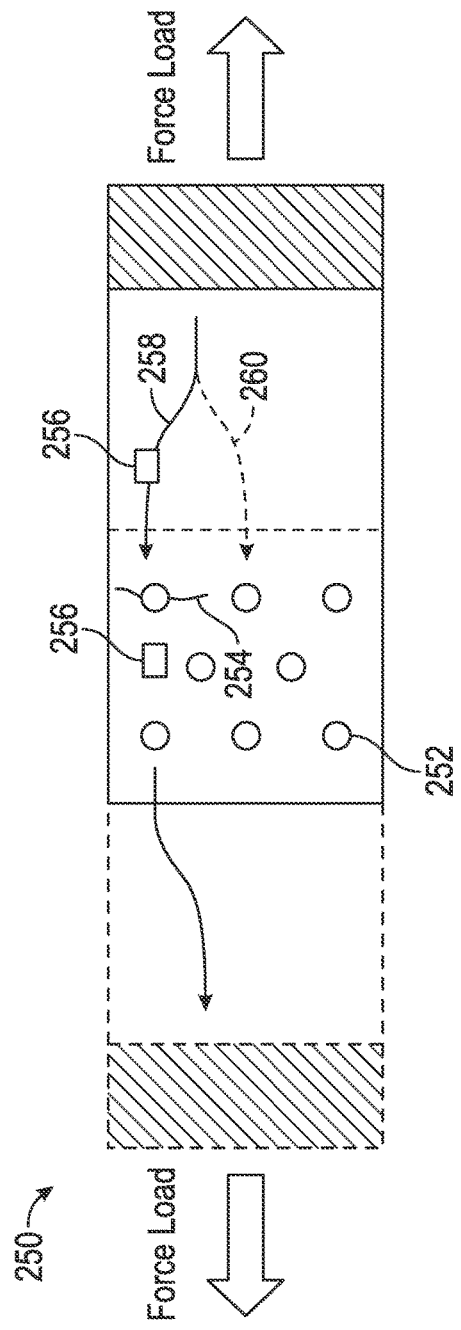

MULTIFUNCTIONAL LOAD AND DAMAGE SENSOR

BACKGROUND

Current damage detection sensors may rely on piezoelectric materials, such as piezoelectric transducers (PZTs) bonded to a structure, for damage detection. For example, a first PZT is excited at high frequencies. A second, nearby PZT sensor measures the response of the first PZT. Any structural damage present in the path between the two PZT actuator/sensors is indicated by changes in the response relative to a baseline version of the response. In this approach, the PZT sensor/actuator is used solely for the purpose of high frequency excitation and damage detection.

BRIEF SUMMARY

An embodiment is directed to a method comprising: obtaining at least one sample of load or load path data from at least one piezoelectric sensor associated with a structure, comparing the at least one sample of data to at least one prior sample of data obtained from the at least one sensor, and providing a status of a health of the structure based on the comparison.

An embodiment is directed to an apparatus comprising: at least one processor, and memory having instructions stored thereon that, when executed by the at least one processor, cause the apparatus to: obtain at least one sample of load or load path data from at least one piezoelectric sensor associated with a structure, compare the at least one sample of data to at least one prior sample of data obtained from the at least one sensor, and provide a status of a health of the structure based on the comparison.

An embodiment is directed to a system comprising: a plurality of piezoelectric sensors configured to generate data pertaining to loads imposed on a structure of an aircraft, a computing device configured to: obtain a first sample of load or load path data from a first of the sensors and at least a second sample of load or load path data from at least a second of the sensors, compare the first sample of data and the at least a second sample of data to one another and to at least one prior sample of data, and provide a status of a health of the structure based on the comparison.

Additional embodiments are described below.

BRIEF DESCRIPTION OF THE DRAWINGS

The present disclosure is illustrated by way of example and not limited in the accompanying figures in which like reference numerals indicate similar elements.

FIG. 2A illustrates an exemplary lap-shear joint;

FIG. 2B illustrates an exemplary lap-shear joint under loading conditions;

DETAILED DESCRIPTION

Figure 1:
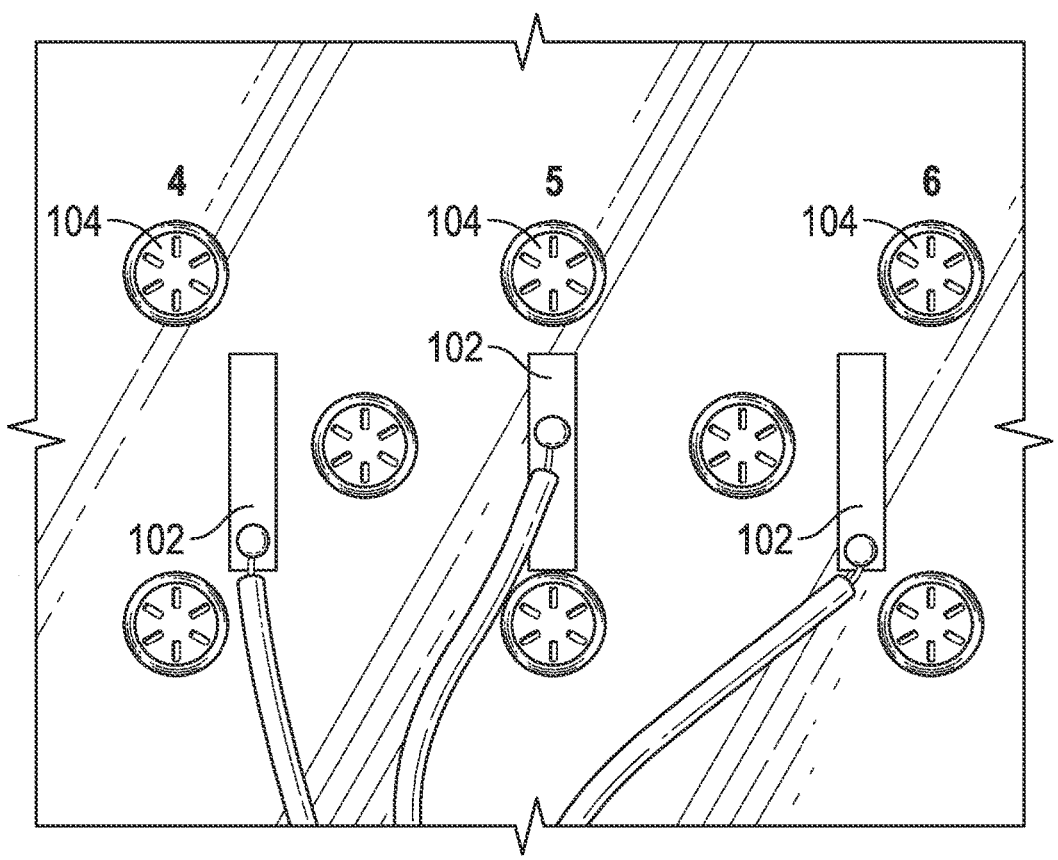
FIG. 1 illustrates an exemplary sensor in accordance with one or more embodiments.

It is noted that various connections are set forth between elements in the following description and in the drawings (the contents of which are included in this disclosure by way of reference). It is noted that these connections in general and, unless specified otherwise, may be direct or indirect and that this specification is not intended to be limiting in this respect. In this respect, a coupling between entities may refer to either a direct or an indirect connection.

Exemplary embodiments of apparatuses, systems, and methods are described for using PZT sensors to sense load, in addition to performing a damage detection function. In some embodiments, a monitoring of a structure may be performed in a passive manner, e.g., the monitoring might not require an external or extra source of excitement to be applied to the structure. In some embodiments, joint health may be monitored based on sensor outputs across a joint. In some embodiments, absolute load magnitude monitoring may be provided. In some embodiments, loads may be monitored during one or more states or regimes of operation. In some embodiments, power self-generated by one or more sensors may be collected or aggregated and used to transmit data or information.

In some embodiments, one or more conventional piezoelectric-based damage sensors may be used as load/strain and load-path sensors. Actual operational structural loading may be utilized to produce an easily measurable output proportional to the underlying strain in a structural member. This output, because it is derived from operation-level structural loading such as, e.g., full flight-level loads, may be most sensitive to load path alteration due to damage. Load path direction may also be sensitive to damage, and the sensor can be configured to provide load path information. By comparing two sensor outputs across joints, the joint health can be monitored. Further, the sensors can be used for absolute load magnitude monitoring.

In some embodiments, a large voltage output proportional to a strain in an underlying structure may be obtained without a need for any external excitation. Such an output may be based on a PZT material's intrinsic strain-electric field coupling. This alleviates the need for well controlled power supplies and precision sensing-circuits (like a Wheatstone bridge) required for strain-gages. This high voltage output also simplifies downstream load/strain path sensing electronics.

Referring to FIGS. 1 and 2A, an embodiment incorporating three PZT sensors 102 is shown. The sensors 102 may measure 0.5"×0.125"×0.015". The sensors 102 may be made of one or more materials, such as lead zirconium titanate, and may include plates (e.g., aluminum plates) measuring 3×4.5" (with a plate thickness of 0.062"). Hi lok rivets 104 may be used in connection with the sensors 102 and rivet holes measuring 0.190" (match machined) may be used. The referenced dimensions and material types are illustrative; other dimensions and/or material types may be used in some embodiments.

Figure 3:
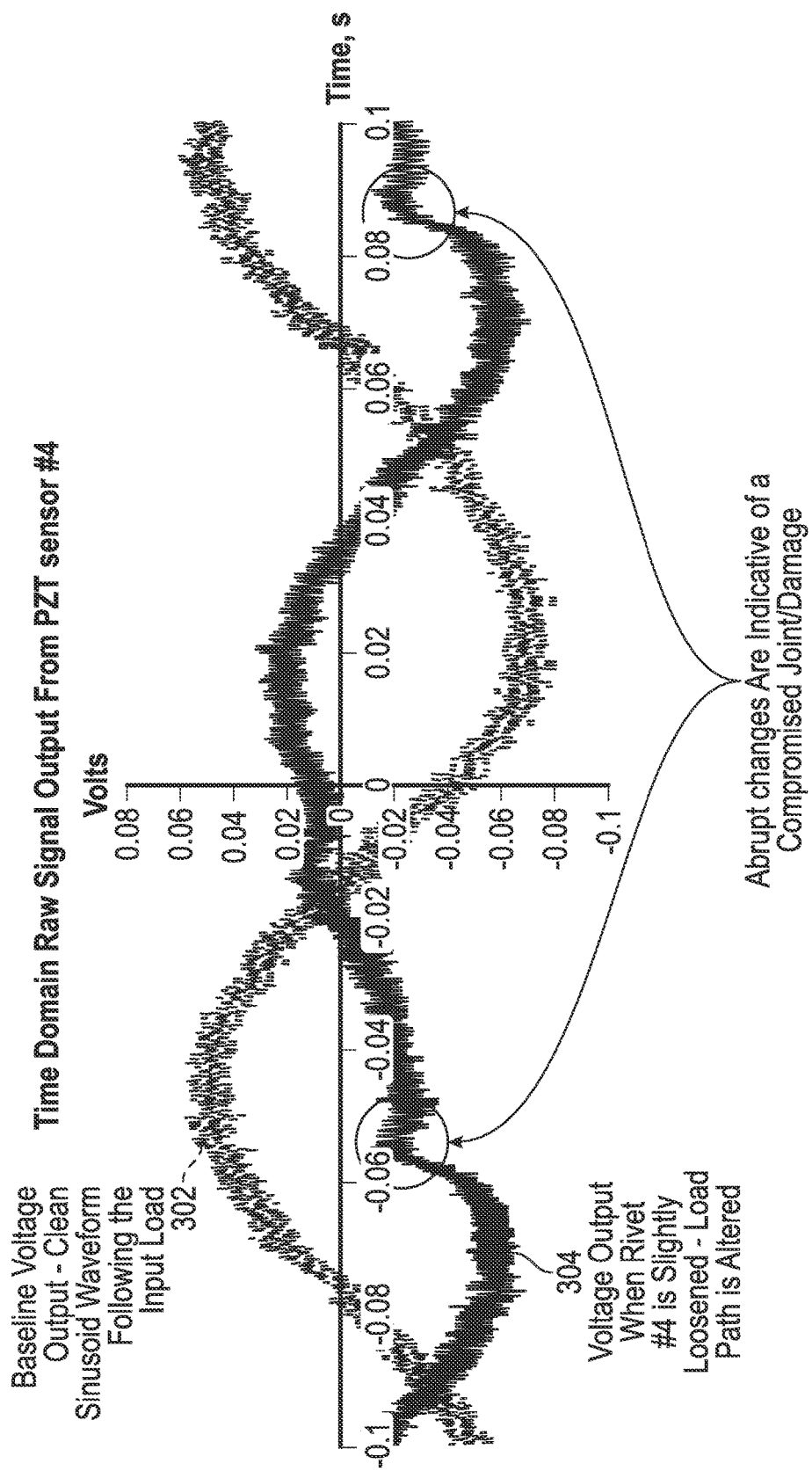
FIG. 3 illustrates waveforms.

The system of FIG. 1 was subject to testing with an application of 0-1000 pounds at 7 Hz and a stress of 0-5000 psi. Referring to FIG. 3, waveforms associated with the testing are shown for a given sensor 102 (e.g., the sensor labeled '4' in FIG. 1, corresponding to the left-most sensor 102). The waveforms may correspond to output voltage signals that are proportional to strain. A first waveform 302 is shown corresponding to a healthy condition of the joint of FIG. 1. As shown, the waveform 302 is a relatively clean and continuous sinusoid with no abrupt changes. A second waveform 304 may be indicative of when the rivet 104 associated with the sensor 102 under test is slightly loosened, resulting in an alteration of a load path. The waveform 304 has abrupt changes (e.g., changes in an amount greater than a threshold) indicative of, e.g., fretting and periodic contact, which may be symptomatic of a compromised joint or damage.

Referring to FIG. 2B, a lap-shear joint 250 in accordance with one or more embodiments is shown. The joint 250 may include one or more bolts or rivets 252, which may serve to connect one or more parts or portions of a structure. One or more of the joint 250 and the bolts/rivets 252 may be subject to damage or cracking, as denoted via reference character 254. The joint 250 may include one or more sensors, such as sensors 256. The sensors 256 may be multi-functional sensors, in the sense that the sensors 256 may be used for purposes of load path monitoring and damage detection.

As shown in FIG. 2B, the joint 250 may be associated with a first or original load path 258 when the joint 250/rivets 252 are free of defects (e.g., when damage/cracking 254 is not present). The joint 250 may be associated with a second or altered load path 260 based on the damage/cracking 254 being present. The first and second load paths 258 and 260 may be different from one another, and this difference may be indicative of the existence and/or extent of the damage/cracking 254.

Figure 2C:
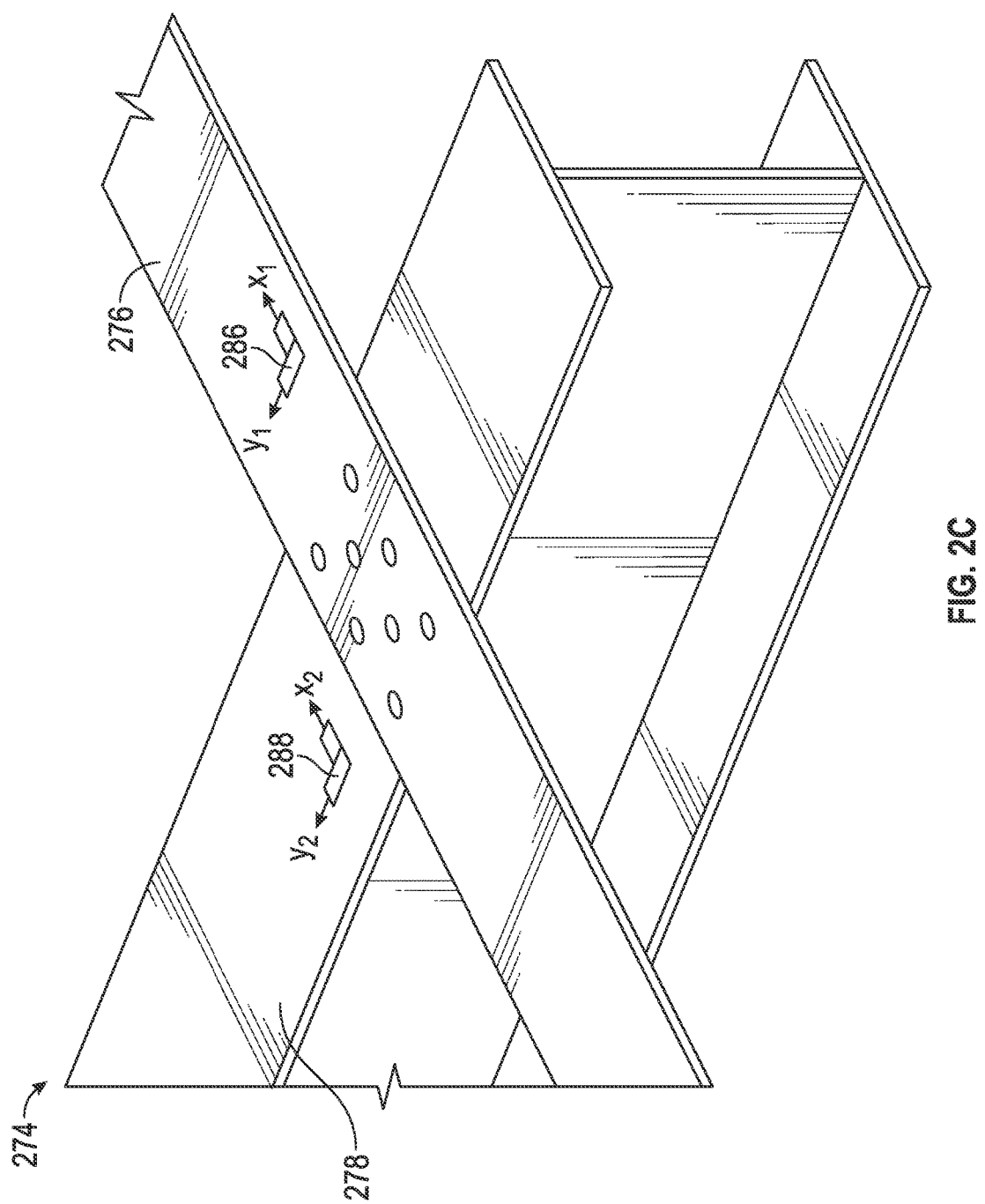
FIG. 2C illustrates the use of a pair of sensors as part of a structure.

Referring to FIG. 2C, a structure 274 is shown. The structure 274 may be composed of one or more members, such as a first member 276 and a second member 278. One or more of the joints of the structure 274, such as a joint coupling the first member 276 and the second member 278, may be highly loaded and/or subjected to cyclic loads causing fatigue.

In some embodiments, the first member 276 may be associated with a first sensor 286 and the second member 278 may be associated with a second sensor 288. The sensors 286 and 288 may be multi-functional sensors. Based on thin PZT layers oriented along two directions (e.g., X and Y as shown in FIG. 2C; $X_1$ and $Y_1$ for sensor 286, and $X_2$ and $Y_2$ for sensor 288), a voltage may be produced proportional to surface strain. The PZTs may act as strain gages (for dynamic loads), which can be used for load estimation. Those same PZTs can be used for active interrogation of critical joints, potentially based on one or more high frequency excitations, in a pitch, catch, or echo mode. The PZT output may be subjected to a notch filter to identify characteristic dynamic response frequencies to improve signal-to-noise ratio (SNR). The outputs of the sensors 286 and 288 may be compared with their baseline outputs. Any differences in the outputs relative to the baseline may serve as an indication of unintended flexibility or damage within the joint. Accordingly, the PZTs may serve as both a damage sensor and a load sensor.

As described above, principles associated with a piezoelectric sensor may be exploited to monitor a health of a structure. The structure might not be affirmatively or actively excited. Moreover, an external or extra power source might not need to be applied, as is typically the case in connection with the use of a strain gauge.

In some embodiments, electricity generated by a piezoelectric sensor may be stored. The stored electricity may be used as a source of power to transmit data (e.g., wirelessly transmit) or information (e.g., load data or information).

As described above, embodiments of the disclosure may be used to monitor load passing through a structure. In this respect, one or more sensors may be configured to measure load in absolute terms. The load may be expressed in one or more units (e.g., pounds).

Information or data regarding loads may be collected during various state or regimes of operation. In an example of use in connection with a rotorcraft, loads may be gathered when, e.g., the rotorcraft is on the ground, when the rotorcraft is flying in a steady-state condition (e.g., no changes being made to flight controls) or during a flight maneuver, etc.

Load information may be analyzed to determine or detect the safety of a structure. For example, load information may be analyzed to determine whether the structure has any cracks or damage.

Load information may be analyzed to determine if there is a need to inspect a structure. For example, if the load information indicates a change in an amount greater than a threshold, a targeted inspection of the structure may be scheduled. In this manner, unnecessary or excessive inspections may be minimized or eliminated.

Load information may be analyzed in connection with a lifetime associated with a structure such as, e.g., an aircraft. For example, predictive algorithms may be used to predict loads that the aircraft or structure would be subject to during operation (e.g., one or more flight regimes). If the actual loads experienced by the structure or aircraft depart from the predicted loads, the difference may serve to shorten or extend the service life of the structure or aircraft before the structure or aircraft is retired from service.

Figure 4:
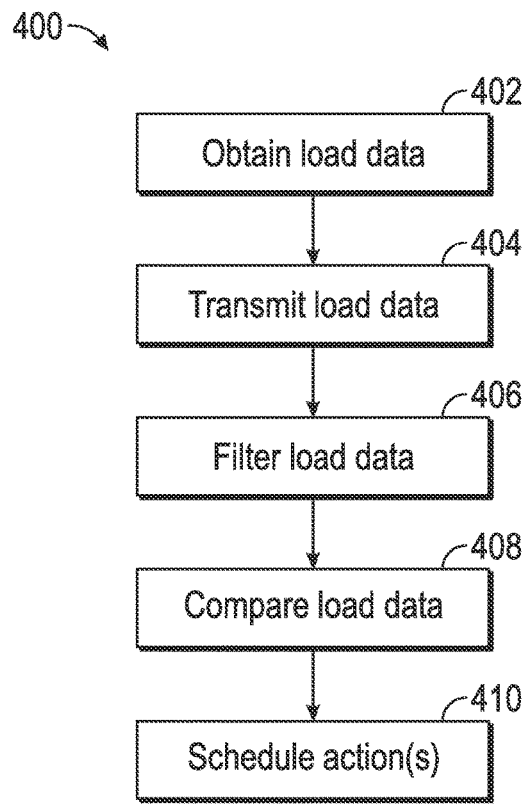
FIG. 4 illustrates a flow chart of an exemplary method.

Turning now to FIG. 4, a flow chart of an exemplary method 400 is shown. The method 400 may be executed in connection with one or more systems, components, or devices, such as those described herein. The method 400 may be used to perform diagnostics or analyses in connection with a structure.

In FIG. 4 another option is to process the data locally and convert it into an actionable output which is then transmitted for diagnostic and prognostic decision making.

In block 402, load data may be obtained. The load data may be obtained from one or more sensors, such as one or more piezoelectric sensors.

In block 404, the load data of block 402 may be transmitted. For example, the load data may be wirelessly transmitted to, e.g., a computing device that is external from an aircraft or other vehicle or structure. The load data may be tagged to identify a particular sensor that the load data originates from. The load data may be tagged to identify a state of a structure (e.g., a critical structure) or aircraft when the load data was taken/sampled.

In block 406, the load data may be filtered. The filtering may be performed to reduce the effect or impact of noise on a given measurement and may be used to obtain load values indicative of the physical world.

In block 408, the load data of block 402 (or the filtered version of block 406) may be compared. The comparison of block 408 may include a comparison between load data obtained from a first sensor and load data obtained from a second sensor. The comparison of block 408 may include a comparison between a current sample of load data and one or more prior samples of the load data in order to gauge the change in the load data over time.

In block 410, one or more actions may be taken or scheduled based on the comparison of block 408. For example, an action may be scheduled if the comparison of block 408 exceeds a threshold. As part of block 410, one or more maintenance or inspection activities may be scheduled. As part of block 410, a predicted safe lifetime associated with a structure or aircraft may be adjusted (e.g., extended or shortened). As part of block 410, the status of the health of a structure or an aircraft may be provided.

The method 400 is illustrative. In some embodiments, one or more of the blocks or operations (or a portion thereof) may be optional. In some embodiments, additional blocks or operations not shown may be included. In some embodiments, the blocks or operations may execute in an order or sequence that is different from what is shown in FIG. 4.

Figure 5:
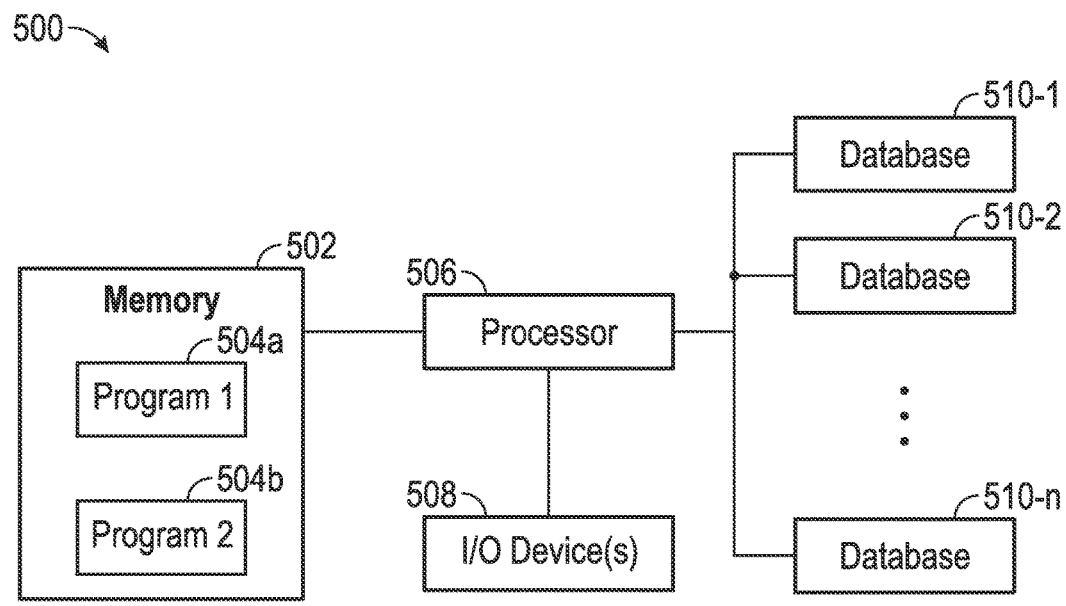
FIG. 5 illustrates an exemplary computing system.

Referring to FIG. 5, an exemplary computing system 500 is shown. Computing system 500 may be part of an aircraft. The system 500 is shown as including a memory 502. The memory 502 may store executable instructions. The executable instructions may be stored or organized in any manner and at any level of abstraction, such as in connection with one or more applications, processes, routines, procedures, methods, etc. As an example, at least a portion of the instructions are shown in FIG. 5 as being associated with a first program 504a and a second program 504b.

The instructions stored in the memory 502 may be executed by one or more processors, such as a processor 506. The processor 506 may be coupled to one or more input/output (I/O) devices 508. In some embodiments, the I/O device(s) 508 may include one or more of a keyboard or keypad, a touchscreen or touch panel, a display screen, a microphone, a speaker, a mouse, a button, a remote control, a control stick, a joystick, a printer, a telephone or mobile device (e.g., a smartphone), a sensor, etc. The I/O device(s) 508 may be configured to provide an interface to allow a user to interact with the system 500.

As shown, the processor 506 may be coupled to a number 'n' of databases, 510-1, 510-2, ... 510-n. The databases 510 may be used to store data, such as data obtained from one or more sensors (e.g., piezoelectric sensors).

The system 500 is illustrative. In some embodiments, one or more of the entities may be optional. In some embodiments, additional entities not shown may be included. In some embodiments, the entities may be arranged or organized in a manner different from what is shown in FIG. 5. For example, in some embodiments, the memory 502 may be coupled to or combined with one or more of the databases 510.

Embodiments of the disclosure may use PZT sensors to sense load (and direction of load) in addition to performing a damage detection function. Actual, operational structural loads may produce a measurable output proportional to underlying strain in a structural member. This output may be derived from full flight-level loads and may be sensitive to load path alteration due to damage. By comparing two sensor outputs across one or more joints, joint health may be monitored. The sensors may be used for absolute load magnitude monitoring. The use of PZTs as damage sensors and load sensors may be combined with a variety of existing damage calculation or characterization algorithms.

Embodiments of the disclosure may utilize a PZT material's intrinsic strain-voltage coupling or relationship to generate a large voltage output proportional to the strain in an underlying structure, potentially without the need for any external excitation. In this respect, well-controlled power supplies and precision sensing-circuits for strain-gages might not be needed. Use of a high voltage output may simplify downstream load/strain path sensing electronics. The sensor may continue to be used for conventional damage monitoring approaches.

Embodiments of the disclosure may be used to provide reliable data and information regarding the operation and use of an aircraft or other vehicle or structure. Such data/information may be available at a reduced cost relative to conventional techniques while at the same time enhancing safety associated with the use of the aircraft or other vehicle or structure.

As described herein, in some embodiments various functions or acts may take place at a given location and/or in connection with the operation of one or more apparatuses, systems, or devices. For example, in some embodiments, a portion of a given function or act may be performed at a first device or location, and the remainder of the function or act may be performed at one or more additional devices or locations.

Embodiments may be implemented using one or more technologies. In some embodiments, an apparatus or system may include one or more processors, and memory storing instructions that, when executed by the one or more processors, cause the apparatus or system to perform one or more methodological acts as described herein. Various mechanical components known to those of skill in the art may be used in some embodiments.

Embodiments may be implemented as one or more apparatuses, systems, and/or methods. In some embodiments, instructions may be stored on one or more computer-readable media, such as a transitory and/or non-transitory computer-readable medium. The instructions, when executed, may cause an entity (e.g., an apparatus or system) to perform one or more methodological acts as described herein.

Aspects of the disclosure have been described in terms of illustrative embodiments thereof. Numerous other embodiments, modifications and variations within the scope and spirit of the appended claims will occur to persons of ordinary skill in the art from a review of this disclosure. For example, one of ordinary skill in the art will appreciate that the steps described in conjunction with the illustrative figures may be performed in other than the recited order, and that one or more steps illustrated may be optional.

What is claimed is:

1. A method comprising:
    obtaining at least one prior sample of data with a piezoelectric sensor associated with a structure, the at least one prior sample being a baseline data point corresponding to no damage to the structure;
    obtaining at least one sample of load and load path data from the piezoelectric sensor associated with the structure;
    comparing the at least one sample of data to the at least one prior sample of data obtained from the sensor, wherein the comparison includes determining a change in load magnitude and a change in load path direction between the at least one sample and the at least one prior sample;
    providing a status of a health of the structure based on the comparison based on load detection and damage detection with the same piezoelectric sensor; and
    scheduling at least one of a maintenance activity and an inspection activity based on the health of the structure.

2. The method of claim 1, further comprising:
    using the at least one sample of data to provide an indication of absolute load.

3. The method of claim 1, wherein the structure is associated with an aircraft, and wherein the at least one sample of data is tagged with a tag based on a state of operation of the aircraft when the at least one sample of data is taken by the piezoelectric sensor.

4. The method of claim 3, wherein the tag indicates at least one of: that the aircraft is on the ground, that the aircraft is flying in a steady-state condition, and that the aircraft is engaged in a flight maneuver.

5. The method of claim 1, further comprising:
    adjusting a safe lifetime associated with the structure based on the at least one sample of data.

6. The method of claim 1, further comprising:
wirelessly transmitting the at least one sample of data based on power obtained from the piezoelectric sensor.

7. The method of claim 1, wherein the at least one sample of data is filtered prior to the comparison with the at least one prior sample of data.

8. The method of claim 1, further comprising a plurality of piezoelectric sensors, wherein the at least one sample of data comprises a plurality of samples of data, and wherein each of the plurality of samples of data is associated with a respective one of the plurality of piezoelectric sensors.

9. The method of claim 8, further comprising:
comparing a first of the plurality of samples of data obtained from a first of the plurality of piezoelectric sensors to a second of the plurality of samples of data obtained from a second of the plurality of piezoelectric sensors to determine that a portion of the structure that bridges the first and second piezoelectric sensors is damaged.

10. The method of claim 1, further comprising:
injecting a voltage at the piezoelectric sensor;
measuring, at a second sensor associated with the structure and located at a distance from the piezoelectric sensor, an induced voltage; and
determining that a portion of the structure is healthy based on determining that the measured voltage at the second sensor deviates from the injected voltage in an amount less than a threshold.

11. The method of claim 10, wherein the piezoelectric sensor is associated with a first member, and wherein the second sensor is associated with a second member, and wherein the portion of the structure comprises a joint that couples the first member and the second member.

12. The method of claim 1, wherein providing a status of a health of the structure includes determining if the change in amount between the at least one sample of data and the at least one prior sample of data is greater than a threshold.

13. An apparatus comprising:
at least one processor; and
memory having instructions stored thereon that, when executed by the at least one processor, cause the apparatus to:
obtain at least one prior sample of data with a piezoelectric sensor associated with a structure, the at least one prior sample being a baseline data point corresponding to no damage to the structure;
obtain at least one sample of load and load path data from the piezoelectric sensor associated with the structure;
compare the at least one sample of data to at least one prior sample of data obtained from the piezoelectric sensor including determining a change in load magnitude and a change in load path direction between the at least one sample and the at least one prior sample; and
provide a status of a health of the structure based on the comparison based on load detection and damage detection with the same piezoelectric sensor.

14. The apparatus of claim 13, wherein the instructions, when executed by the at least one processor, cause the apparatus to:
use the at least one sample of data to provide an indication of absolute load.

15. The apparatus of claim 13, wherein the structure is associated with an aircraft, and wherein the instructions, when executed by the at least one processor, cause the apparatus to:
tag the at least one sample of data with an identification of the piezoelectric sensor and with an identification of a state of operation of the aircraft or other critical structures when the at least one sample of data is taken by the piezoelectric sensor.

16. The apparatus of claim 13, wherein the instructions, when executed by the at least one processor, cause the apparatus to:
wirelessly receive the at least one sample of data based on power obtained from the piezoelectric sensor.

17. The apparatus of claim 13, further comprising a plurality of piezoelectric sensors, and wherein the at least one sample of data comprises a plurality of samples of data, and wherein each of the plurality of samples of data is associated with a respective one of the plurality of piezoelectric sensors.

18. The apparatus of claim 17, wherein the instructions, when executed by the at least one processor, cause the apparatus to:
compare a first of the plurality of samples of data obtained from a first of the plurality of piezoelectric sensors to a second of the plurality of samples of data obtained from a second of the plurality of piezoelectric sensors to determine that a joint associated with the structure that bridges the first and second piezoelectric sensors is damaged.

19. The apparatus of claim 13, wherein providing a status of a health of the structure includes determining if the change in amount between the at least one sample of data and the at least one prior sample of data is greater than a threshold.

* * * * *